US010226540B2

(12) United States Patent
Dickner et al.

(10) Patent No.: US 10,226,540 B2
(45) Date of Patent: Mar. 12, 2019

(54) STERILIZATION MACHINE AND METHOD FOR STERILIZING PACKAGING CONTAINERS

(71) Applicant: Tetra Laval Holdings & Finance S.A., Pully (CH)

(72) Inventors: Jonas Dickner, Påarp (SZ); Håkan Mellbin, Hörby (SE); Roger Lindgren, Sövde (SE); Mats Åkesson, Malmö (SE)

(73) Assignee: TETRA LAVAL HOLDINGS & FINANCE S.A., Pully (CH)

( * ) Notice: Subject to any disclaimer, the term of this patent is extended or adjusted under 35 U.S.C. 154(b) by 239 days.

(21) Appl. No.: 15/119,577

(22) PCT Filed: Jan. 21, 2015

(86) PCT No.: PCT/EP2015/051075
§ 371 (c)(1),
(2) Date: Aug. 17, 2016

(87) PCT Pub. No.: WO2015/124358
PCT Pub. Date: Aug. 27, 2015

(65) Prior Publication Data
US 2017/0049914 A1    Feb. 23, 2017

(30) Foreign Application Priority Data

Feb. 19, 2014   (SE) ........................................ 1450198

(51) Int. Cl.
*G01N 21/00*    (2006.01)
*A61N 5/00*    (2006.01)
(Continued)

(52) U.S. Cl.
CPC ................ *A61L 2/087* (2013.01); *B65B 3/00* (2013.01); *B65B 55/08* (2013.01); *G21K 5/02* (2013.01);
(Continued)

(58) Field of Classification Search
CPC . A61L 2/208; A61L 2/00; A61L 12/00; B67C 7/00
(Continued)

(56) References Cited

U.S. PATENT DOCUMENTS 8,834,808 B2 * 9/2014 Drenguis ................ A61L 2/208
134/61
2011/0012032 A1    1/2011 Bufano et al.
(Continued)

FOREIGN PATENT DOCUMENTS

| EP | 2 371 397 A1 | 10/2011 |
|----|----|----|
| WO | WO 20091139074 A1 | 11/2009 |
| WO | WO 2013/092735 A1 | 6/2013 |

OTHER PUBLICATIONS

International Search Report (PCT/ISA/210) dated May 13, 2015, by the European Patent Office as the International Searching Authority for International Application No. PCT/EP2015/051075.
(Continued)

*Primary Examiner* — Monzer R Chorbaj
(74) *Attorney, Agent, or Firm* — Buchanan Ingersoll & Rooney PC

(57) ABSTRACT

Sterilization apparatus for sterilizing packaging containers, the sterilization apparatus comprising a first carousel for supporting a plurality of sterilization devices, the sterilization devices being adapted to sterilize an interior of the packaging containers by electron beam irradiation, and a transport system for transporting the packaging containers, the transport system comprising a second carousel coaxial
(Continued)

Figure 1:
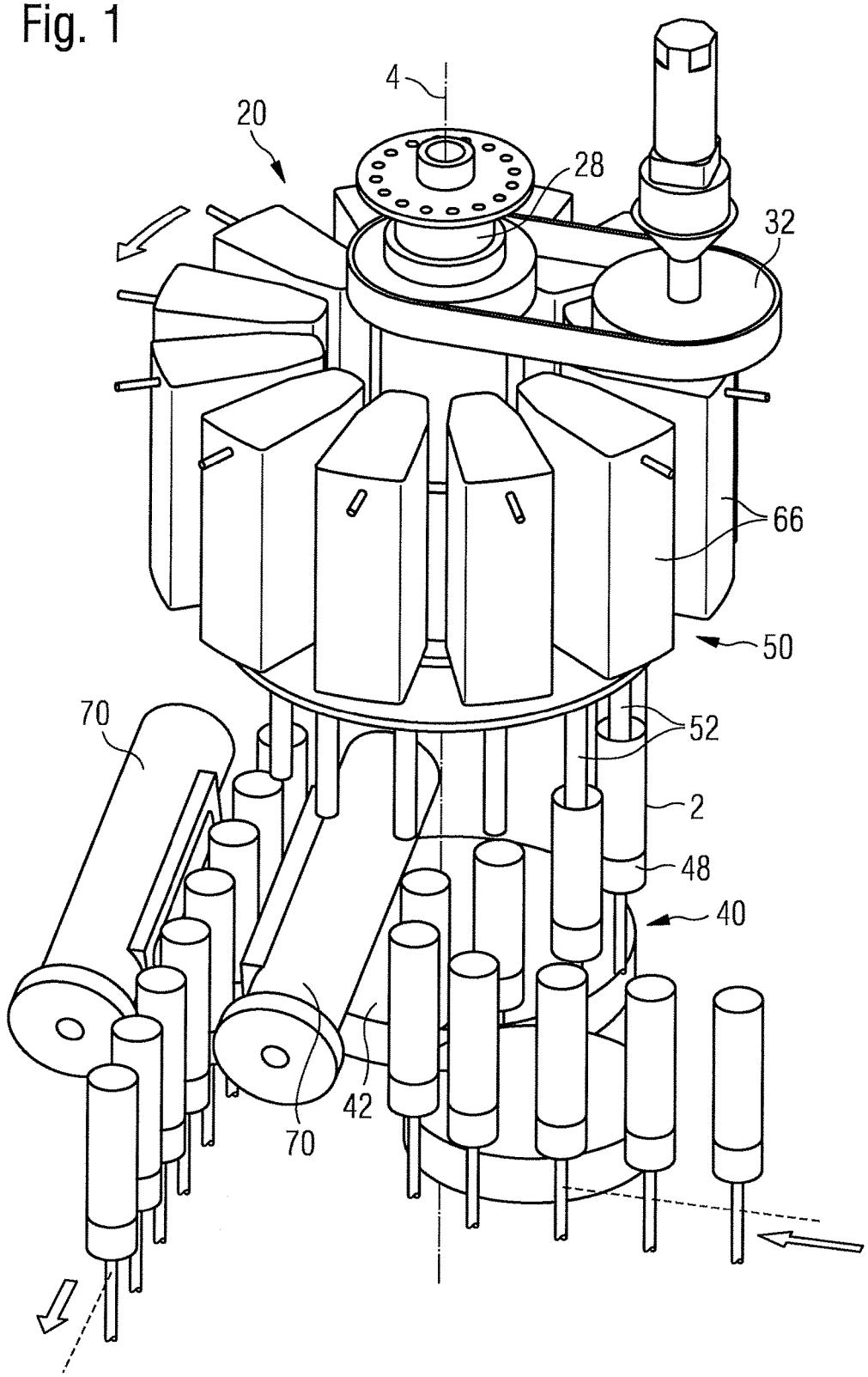

with the first carousel, wherein the first carousel comprises a first rotatable shaft and the second carousel comprises a separate second rotatable shaft coaxial with the first rotatable shaft.

19 Claims, 3 Drawing Sheets

(51) Int. Cl.
*A61L 2/00* (2006.01)
*A61L 2/08* (2006.01)
*B65B 55/08* (2006.01)
*H01J 37/24* (2006.01)
*B65B 3/00* (2006.01)
*G21K 5/02* (2006.01)
*H01J 37/16* (2006.01)
*H01J 37/07* (2006.01)

(52) U.S. Cl.
CPC .......... *H01J 37/165* (2013.01); *H01J 37/242* (2013.01); *A61L 2202/23* (2013.01); *H01J 37/07* (2013.01)

(58) Field of Classification Search
USPC ....... 422/292, 300, 302; 134/44, 61; 99/316; 250/455.11, 492.1
See application file for complete search history.

(56) References Cited

U.S. PATENT DOCUMENTS

| | | |
|---|---|---|
| 2011/0084221 A1 | 4/2011 | Eguchi et al. |
| 2012/0230865 A1 | 9/2012 | Graffin et al. |
| 2014/0369885 A1 | 12/2014 | Krueger |

OTHER PUBLICATIONS

Written Opinion (PCT/ISA/237) dated May 13, 2015, by the European Patent Office as the International Searching Authority for International Application No. PCT/EP2015/051075.

Swedish Office Action dated Oct. 6, 2014, issued by the Swedish Patent Office in the corresponding Swedish Patent Application No. 1450198-5. (8 pages).

* cited by examiner

STERILIZATION MACHINE AND METHOD FOR STERILIZING PACKAGING CONTAINERS

The invention relates to a sterilization apparatus and a method for sterilization packaging containers.

In the food industry it is common practice to pack liquid and partly liquid food products in packaging containers. Such packaging containers can for example be made of a plastic material such as for instance PET, or be made of a laminated carton material. With regard to the later a common type of laminated carton material is the ones that comprises a core layer of paper or paperboard and one or more barrier layers of, for example, polymer material or aluminium foil. An increasingly common packaging type is the "carton bottle" manufactured in a filling machine in that packaging blanks of the above-described packaging laminate are formed and sealed as a sleeve. Said sleeve is closed in one end in that a top of thermoplastic material is injection moulded directly on the sleeve end portion. The sheets of packaging laminate may be cut from a magazine reel of packaging laminate.

Before the packaging container is filled with the food product, in particular if filling takes place at ambient temperature, the packaging container needs to be sterilized. Sterilization is a term referring to any process that eliminates or kills microbial life, including transmissible agents such as for example fungi, bacteria, viruses and spores, which may be present on a surface of the packaging material or in a product. In the (food) packaging industry this is generally referred to as aseptic packaging, i.e. packaging sterilized products in sterilized packaging containers, i.e. keeping both the product and the packaging container free form living germs and microorganisms, so that the freshness of the product can be preserved without special cooling requirements, i.e. so that sterility can be maintained inside a packaging container although it is stored in ambient temperature. In this context the term "commercially sterile" is also commonly used and means in general the absence of microorganisms capable of growing in the food at normal non-refrigerated conditions at which the food is likely to be held during manufacture, distribution and storage. In this patent application the word "sterile" refers to a condition being at least commercially sterile.

A conventional way of sterilizing packaging containers is a chemical sterilization, in particular using hydrogen peroxide, preferably in gas phase. However, this process has the drawback that residues of the chemical substance might remain on a surface of the container.

Another known way of sterilizing packaging containers is through radiation, in particular, using electron beams. EP 2 371 397 A1 describes a sterilization machine comprising a plurality of sterilization devices adapted to be inserted into the containers for sterilizing the interior of the containers. The containers and the sterilization devices are arranged on a common rotary support structure which holds the containers and the sterilization devices in a mutually aligned position and rotates them along a circular path. The containers are lifted relative to the sterilization devices so that a rod-shaped sterilization element is inserted into the respective container for sterilizing the interior or the container. Another example of a sterilization device for sterilization of packaging containers is described in the international application No. PCT/EP2013/076870 filed by the applicant.

Nonetheless, there's still a need to provide an improved sterilization apparatus and method for sterilizing packaging containers allowing for a particularly safe and economical sterilization.

The invention proposes a sterilization apparatus according to claim 1 and a method for sterilizing packaging containers according to claim 17. Embodiments and several aspects of the invention are defined in the dependent claims and the following description, in particular in connection with the attached drawings.

Figure 2:
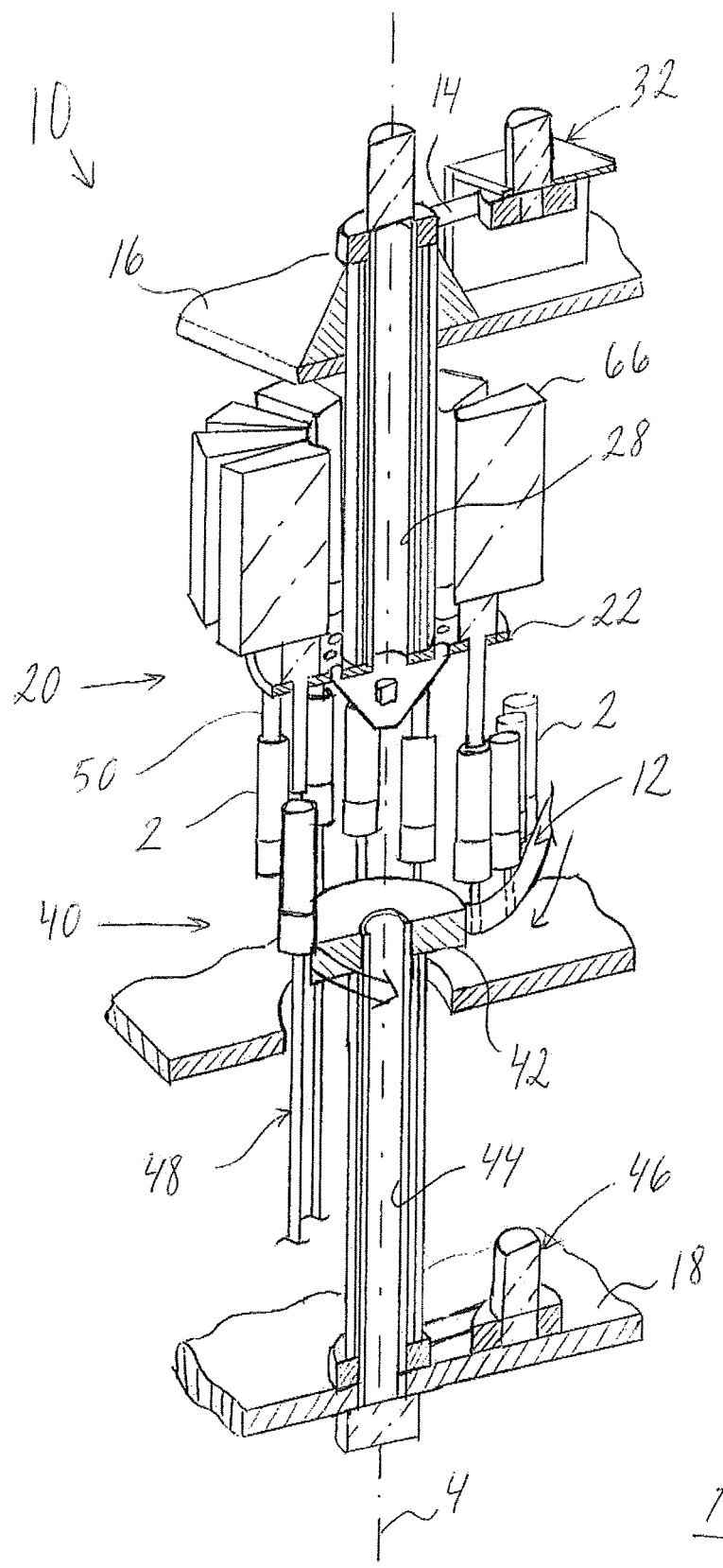
Figure 3:
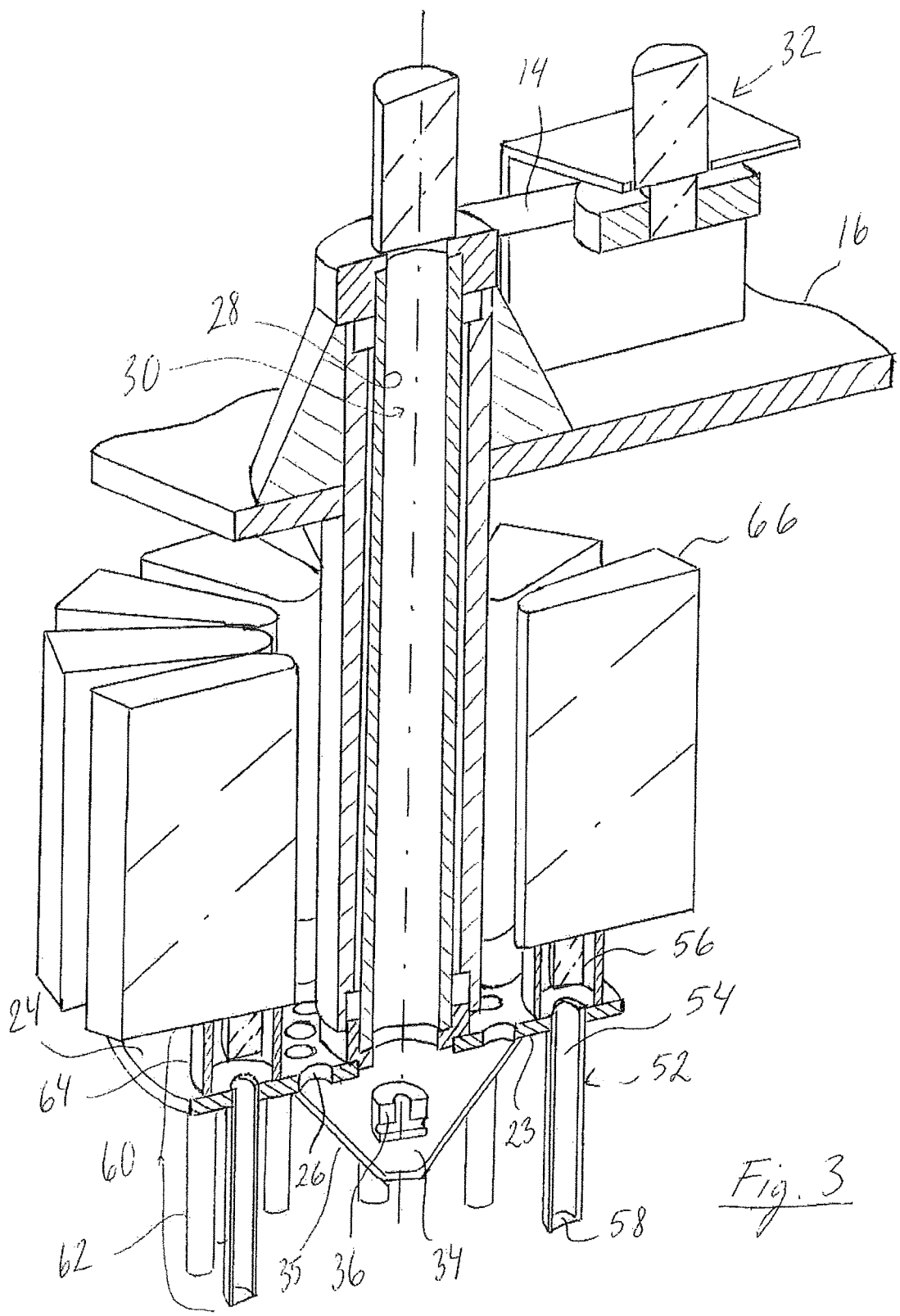

The invention will now be further described in connection with the attached drawings in which:

FIG. 1: shows a perspective view of a first embodiment of an inventive sterilization apparatus;

FIG. 2: shows a perspective view of a second embodiment of an inventive sterilization apparatus cut along a plane through the common axis of rotation of the carousels; and FIG. 3: shows the upper carousel of FIG. 2 in more detail.

Equal or corresponding elements are denominated by the same reference numerous in all figures. The features described in connection with the different embodiments can be combined as far as technically possible. Some cross sectional surfaces are provided with dashed-dotted lines. This is to illustrate that a cross section has been made through a feature but that details of the interior of the feature is not shown in detail.

The sterilization apparatus according to the invention for sterilizing packaging containers comprises a first carousel for supporting a plurality of sterilization devices, the sterilization devices being adapted to sterilize an interior of the packaging containers by electron beam irradiation, and a transport system for transporting the packaging containers, the transport system comprising a second carousel coaxial with the first carousel. The first carousel comprises a first rotatable shaft and the second carousel comprises a second rotatable shaft being spaced apart from the first rotatable shaft. In an embodiment both shafts may share a common rotational axis.

The term carousel shall include any type of movable device, for example conveyor chains or plate, belts, wheels and the like. The movement along a trajectory of the carousel may comprise a pure rotational movement but is not limited thereto. It may also comprise a translational movement or a combination of rotational and translational movement.

The term "packaging container" shall not be limited to container for liquid or solid food, but is used for convenience purposes only. Generally any container, which needs to be sterilized, is suitable for this purpose and shall fall under this term, including, but not limited to, container for medical drugs, for medical devices, for liquid, semi-liquid or solid food, for storing biological material or organic substances.

The term "sterilization" in this context means the sterilization of a surface of an object to be sterilized and/or,—if the object contains an interior part—, the sterilization of said interior part.

The surface of the object may comprise the inner surface of the object, the interior and the outer surface or parts thereof of the object. The inner surface of the packaging container is the surface being in contact with food, or general the material to be filled into the container. According to the invention, the plurality of sterilization devices is adapted to sterilize the inner surface and the interior of the container. In a further embodiment it is also adapted to sterilize part of the outer surface of the container.

A basic idea of the invention is to provide separate and/or separated carousels for the sterilization devices and the packaging containers, respectively. The first carousel is intended for supporting the sterilization devices and the second carousel is a part of a transport system for transporting the packaging containers along a preferably circular path. The interior sterilization of the containers takes place during transportation of the containers along the circular path. The second carousel may for example either hold the containers directly or guide a container conveyor, such as a chain or belt conveyor, along a preferably circular path.

Each of the carousels may comprise a rotatable wheel or plate connected to a shaft in a rigid manner so that the wheel or plate and the shaft rotate together. The first rotatable shaft can be a drive shaft for rotating the wheel or plate of the first carousel and the second rotatable shaft is preferably a drive shaft for rotating the wheel or plate of the second carousel.

The separate carousels with separate drive shafts allow for a greater flexibility of operation and a better utilization of the available space in the sterilization machine as compared to the known composite carousel with single drive shaft. Because the carousels are not interconnected by a single common drive shaft, it is generally possible to operate the carousels independently of each other. Such arrangement allows for adjustment of one of the plate with respect to the other. Moreover, an additional free space is generated between the carousels, in particular between the first and second rotatable shafts, which can be used so that the compactness of the machine can be enhanced and/or the arrangement of components within the machine can be improved.

The sterilization devices are preferably adapted to be at least partly inserted into a respective packaging container to be sterilized, in particular through an open top or bottom of the packaging container. In an embodiment, the sterilization devices is inserted into the container along a substantially vertical movement direction during rotation of the sterilization devices and the packaging containers about a common rotational axis defined by the first and second rotary shafts. It may be preferred according to the invention that the first carousel is an upper carousel and the second carousel a lower carousel.

In an embodiment of the invention, the sterilization apparatus comprises a first driving device for rotating the first carousel. The first driving device is adapted to rotate the first drive shaft (first rotary shaft) and may in particular be a rotary drive and more preferably an electric motor. The first driving device may be arranged on a stationary frame element, in particular on a side of the sterilization devices opposite the second rotational shaft. More preferably, the driving device is arranged in a plane above the sterilization devices.

According to an embodiment the first driving device is adapted to drive and rotate the first and second carousel. For this purpose, the first driving device is in operative connection with the first and the second rotatable shafts. For instance, the first driving device may comprise a third shaft arranged substantially parallel to the first and second shaft but spaced apart from them. Such shaft may be coupled to the first and/or second shaft by coupling means, i.e. by a conveyor belt, a band, V-belt, chain, gear drive, spiral bevel gear, sleeve or torsion clutch and the like.

The operative connection to any of the shafts may also comprise a synchronizing device for synchronizing the rotation or movement of the first carousel with the second carousel and vice versa.

In an alternative embodiment of the invention, the sterilization machine comprises a second driving device for rotating the second carousel. The second driving device is adapted to rotate the second drive shaft (second rotary shaft) and may in particular be a rotary drive and more preferably an electric motor. The second driving device may be arranged on a stationary frame element, in particular on a side of the packaging containers opposite the first rotational shaft. More preferably, the motor is arranged in a plane below a conveying path of the packaging containers. In such concept of the invention, the sterilization machine comprises separate driving devices for driving the first carousel and the second carousel, wherein a first driving device is adapted to rotate the first rotatable shaft and a second driving device is adapted to rotate the second rotatable shaft.

In an embodiment the second driving device is adapted to drive the second carousel independently of the first carousel. In other words, the second driving device may be operated independently of the first driving device, so that it is for example possible to rotate the second carousel (with the sterilization devices) while the first carousel is standing still. The advantage of this embodiment is that an overheating of the packaging containers by the sterilization devices can be efficiently prevented in case of an interruption of the movement of the containers. It is in particular not necessary to stop the operation of the sterilization devices which are generally and preferably operated continuously.

For sterilization purposes, i.e. during regular operation of the sterilization apparatus, the sterilization apparatus may comprise synchronization device for synchronizing a rotational movement of the first carousel and the second carousel. The synchronization device is adapted to synchronize the speed of the first and second carousel and maintain a relative fixed position such that the longitudinal axes of the packaging containers and the sterilization devices are aligned. I.e. a longitudinal axis of each packaging container is aligned with a longitudinal axis of one of the sterilization devices. The packaging containers and the sterilization devices are preferably transported along a sterilization path with their respective longitudinal axis being aligned with each other. The sterilization path is at least partly circular.

The synchronization device is preferably adapted to be switched on and switched off, i.e. be put in operation and out of operation, preferably through a control unit and/or by an operator. In normal operation it may be used to keep the position of packaging containers aligned with the position of sterilization device and may be controlled by a control unit comprising sensors for measuring the positions and calculation units using feedback loops to achieve such alignment. The synchronization can be turned off in case of an unintentional interruption of the transport system transporting the packaging containers, such that the sterilization devices may keep rotating even during a downtime of the transport system, i.e. a standstill of the packaging containers. The control unit for controlling the synchronization device is preferably adapted to prevent the sterilization devices to be standing still while they are operating, i.e. they are either turned off or they are kept rotating.

In order to provide the possibility to interrupt the synchronization of the carousels, there is preferably no permanent and/or forced synchronisation, in particular no permanent and/or rigid mechanical connection interconnecting—for a synchronized movement of the carousels—the first and second carousels.

The independent rotation of the sterilization devices also allows for testing the sterilization devices before a start up of the sterilization machine and/or during an interruption.

Such testing can, for example, be done by passing the rotating sterilization devices along a stationary sensor device arranged on the sterilization machine while the packaging containers are not moving.

In another embodiment of the invention the first rotatable shaft is constructed as a hollow shaft having an interior channel for receiving at least one utility line for the sterilization devices and a distribution chamber is arranged at an end of the first rotatable shaft facing the second rotatable shaft.

The distribution chamber may comprise a housing and at least one exit opening for a utility line. This embodiment allows for an easy connection of the sterilization devices to a utility system, for example an electrical system, and/or a cooling system, and/or a data communication system. The utility lines or supply lines may be routed from the sterilization devices to the utility system through the central rotatable shaft of the first carousel, in particular via the distribution chamber.

Utility lines may comprise an electrical connection, like one or more wires for electrical current or a connection for a cooling medium, i.e. a pipe. The utility line or lines are coupled to a utility system on one end of the shaft and to the sterilization devices. There might be a plurality of individual utility lines routed through the shaft, each of those assigned to one of the plurality of sterilizing devices. Alternatively there might be a common utility line, i.e. for a cooling medium routed through the shaft. Said common utility line might be separated in the distribution chamber to supply the individual sterilization devices.

In another embodiment, a distribution device for distributing at least one utility to the sterilization devices is arranged within the distribution chamber. The distribution device may be connected to the utility line from the shaft. The distribution chamber preferably encloses the distribution device such that it is separated from a sterilization chamber or zone where the electrons exit the sterilization devices and where the sterilization takes place.

In an embodiment, the distribution chamber closes and covers the interior channel of the first rotatable shaft towards the sterilization zone so that the introduction of non-sterile elements (dirt etc.) from the channel to the sterilization zone is essentially prevented. The distribution device can in particular be adapted for distributing utilities such as electricity/power and/or a cooling fluid to the respective sterilization devices. Also data communication can make use of the distribution device for data transfer between the sterilization devices and a control unit.

In a particularly embodiment, the housing of the distribution chamber completely encloses the distribution chamber on the first side of the carrier plate. By that, the channel of the first rotatable shaft and/or the interior of the distribution chamber has no direct connection to the sterilization zone on the first side of the carrier plate.

In yet another embodiment of the invention, the distribution device includes a swivel. The swivel, which comprises a rotary connection between two elements of the distribution device, has at least one inlet connection for a utility line from the utility system and one or more outlet connections for a utility line (utility lines) to the respective sterilization devices. The swivel allows for a rotational movement of the inlet connection relative to the outlet connection. Therefore, the at least one utility line routed through the channel of the first rotational shaft can be stationary, while the utility lines to the sterilization devices can rotate.

In another embodiment of the invention, the first carousel comprises a rotatable carrier plate which carries the sterilization devices. In one embodiment, the sterilization devices can be attached to the carrier plate on first side facing the second carousel.

Alternatively the distribution chamber is arranged at a first side of the carrier plate facing the second carousel and the sterilization devices are arranged at least partly on a second side of the carrier plate. For instance, a first portion of each of the sterilization devices can be arranged on the first side, a second portion is arranged on a second side of the carrier plate opposite the first side. By this arrangement, the carrier plate separates the distribution chamber from a portion of the sterilization devices, allowing using additional space for the devices, otherwise occupied by the distribution chamber.

The second side of the carrier plate which can be regarded a non-sterile area, may therefore receive the utility lines for the sterilization devices. In the particular embodiment disclosed earlier, the sterilization devices are preferably attached to the carrier plate such that they extend through the carrier plate and an electron exit window is arranged on the first side of the carrier plate and a power device of the sterilization device, in particular a high voltage power device, is arranged on the second side. A connection interface for connecting to the utility line is preferably arranged on the second side of the carrier plate. The connection interface of the sterilization device may, for example, include an electrical interface and/or an interface for a cooling fluid.

In another embodiment, the distribution chamber is cup-shaped and/or has a conical shape. A lower-diameter portion of the distribution chamber preferably faces the second carousel and a larger-diameter portion of the distribution chamber preferably faces the first carousel, in particular the carrier plate. The larger-diameter portion of the distribution chamber preferably has a diameter which is greater than an outer diameter of the first rotatable shaft.

The carrier plate is preferably provided with one or more through-holes providing a connection between the interior of the distribution chamber and the second side of the carrier plate. The at least one through-hole is preferably located in a diameter portion of the carrier plate between the outer circumference of the first rotatable shaft and the inner circumference of the distribution chamber housing in contact with the carrier plate. Alternatively the distribution chamber may comprise opening or through holes at positions aligned with positions of the carrier plate. By this arrangement, utility lines may easily be routed through the first rotatable shaft to the first side of the carrier plate and back to the second side where they can be connected to the sterilization devices.

The distribution chamber may be provided with a radiation shielding, in particular against X-rays. In the following, the term X-ray includes all kinds of electromagnetic radiation and emissions generated during operation of the apparatus, including but not limited to electron collision radiation. The housing of the distribution chamber can for example be constructed from a shielding material such as lead, tungsten, steel or an alloy thereof. The shielding provides a protection of the elements arranged within the distribution chamber such as the distribution element from radiation during operation of the sterilization devices. In addition, the radiation shielding may also provide an efficient radiation protection of the power device, in particular if the radiation shielding has a conical shape.

In another embodiment, at least one fixed second sterilization device is arranged between the first carousel and the second carousel, in particular for sterilizing an outer surface of the packaging containers. The second sterilization device may in particular be arranged along a conveying path of the packaging containers and extend along an entry or exit point of the packaging containers to or from the second carousel. In or more embodiments two second sterilization devices are arranged with their electron exit windows facing each other. They are arranged at a distance from each other such that a gap for packaging containers are formed between them. Their electron clouds form a unified electron cloud filling the gap. The packaging containers are transported in the gap and are thereby sterilized on their outer surface. In one or more embodiments only one second sterilization device is provided, and the packaging container are rotated around their own axes when passing the electron exit window, in order to obtain full sterilization of the outer surface. The second sterilization devices may be stationary.

In a embodiment the at least one second sterilization device is adapted to perform an exterior sterilization of the packaging containers a least partly overlapping with the interior sterilization. That means an area of the at least one second sterilization device, in which an object is sterilized overlaps at least partly with an area, in which an object is sterilized by one of the plurality of first sterilization devices. Therefore, the second sterilization device extends at least partly between the first carousel and the second carousel and may also at least partly extend between the first rotatable shaft and the second rotatable shaft. In such embodiment the at least one second sterilization device is arranged at least partly in the space between the first and second shaft.

A simultaneous interior and exterior sterilization can be achieved in that the second sterilization device is adapted to create a sterilization cloud of electrons at least partly overlapping with a sterilization cloud of a first sterilization device.

The second sterilization device preferably has a longitudinal axis being inclined to the rotational axis of the first and/or the second rotatable shaft, for example between 45 degree and 90 degree, or more particular between 60 degree and 80 degree. In an embodiment is substantially transversal to the rotational axis.

Another aspect of the invention is related to a method for sterilizing a plurality of packaging containers, the method comprising the steps of rotating a first carousel supporting a plurality of sterilization devices which are adapted to sterilize an interior of the packaging containers by electron beam irradiation, and transporting the packaging containers by means of a transport system comprising a second carousel which is coaxial with the first carousel, wherein the first carousel comprises a first rotatable shaft, the second carousel comprises a separate second rotatable shaft coaxial with the first rotatable shaft and the first carousel is rotated by means of a first driving device connected to the first rotatable shaft for rotation thereof. The method can in particular be carried out in an inventive sterilization machine and provides the effects and advantages discussed in connection therewith.

FIG. 2 illustrates a first embodiment of the invention. The sterilization apparatus 10 comprises a frame (not shown) having an upper support element 16 and a lower support element 18. A first carousel 20, which in the shown embodiments is an upper carousel, is supported by the upper support element 16. A second carousel 40, which is a lower carousel, is supported by the lower support element 18. The upper carousel 20 and the lower carousel 40 are rotatable about a common rotation axis 4, which is a vertical axis.

The first carousel 20 comprises a rotary carrier plate 22 which supports a plurality of first sterilization devices 50 that are adapted to sterilize an interior of a packaging container 2 by electron irradiation. The first sterilization devices 50 are arranged on a circumference of the carrier plate 22 which is preferably a circular plate. The first carousel 20 further comprises a first rotatable shaft 28. Shaft 28 is connected on one side to the carrier plate 22 in a fixed manner and coupled with its housing on the other side to support element 16. Thus, first rotatable shaft 28 is supported by the upper support element 16 in a rotatable manner.

The first rotatable shaft 28, which can also be called a drive shaft, is driven by a first driving device 32 in a rotating manner. First driving device 32 is coupled to shaft 28 by a conveyor band 14 having teeth, griping into a tooth wheel attached to shaft 28. Therefore, the carrier plate 22 can be rotated through operation of the first driving device 32. The first driving device 32 is mounted on the upper support element 16 of the frame.

The second carousel 40 comprises a rotary wheel or plate 42 for guiding and/or transporting the packaging containers 2 along a circular transportation path such that each container can be aligned with one of the sterilization devices 50 during its transportation along the transportation path. The wheel 42 can be a rotary carrier or guide wheel 42. It can for example directly hold the packaging containers 2 or as in this embodiment be engaged with a conveyer 12 which conveys and/or holds the packaging containers 2.

A second rotatable shaft 44 is connected to the wheel 42 in a fixed manner. The second rotatable shaft 44, which can be called a second drive shaft, is driven by a second driving device 46 in a rotating manner. The second driving device is connected to second shaft 44 in a similar manner as the first driving device. Therefore, through operation of the second driving device the guide wheel 42 can be rotated. The second driving device 46 is mounted to the lower support element 18 of the frame 14. The second rotatable shaft 44 is supported in a rotatable manner by the lower support element 18. As can be seen from FIG. 2, both driving devices are mounted on the respective plates facing outwards.

In this embodiment, the first rotatable shaft 28 and the second rotatable shaft 44 are coaxial with each other and rotate about a common rotation axis 4. Carrier plate 22 is connected to a lower end portion of the first rotatable shaft 28, and wheel 42 is connected to an upper end portion of the second rotatable shaft 44. The shafts 28, 44 are separated by a gap. The distance between the shafts 28 and 44 corresponds to at least the height of the packaging containers 2, preferably at least twice the height of the packaging containers 2. The first carousel 20 and the second carousel 40 can be driven independently of each other by the respective driving devices 32 and 46.

The sterilization apparatus 10 further comprises a synchronization device (not shown) for a synchronizing the rotational movement of the first carousel 20 with the rotational movement of the second carousel 40 or vice versa. Such synchronization device can for example be a mechanical synchronization device. However, the synchronization device comprises preferably a control unit, which measures any deviation in the alignment. That can be done for example by measuring the position between the first and second carousel, either directly or indirectly using the position of the sterilizing elements and the containers. In an example sensors are continuously measuring position markers on the wheel 42 and plate 22 to compare those with a set position. Any deviation resulting from said measurement is fed to the control unit for processing. Alternatively or in addition, rotational speed can be measured.

The control unit comprise one or more feedback loops to compensate the deviation and synchronize the operations of the first and second driving device 32, 46. In operation, one of the devices may accelerate or decelerate as to reduce any measured deviation until the position of sterilizing devices and containers are realigned.

In addition, the synchronization device is adapted to be put out of operation so as to allow the first carousel 20 and the second carousel 40 to be driven independently of each other. Therefore, the first carousel 20 and the second carousel 40 can be selectively driven in a synchronized manner or in a non-synchronized manner. In particular, it is also possible to only drive one of the carousels i.e. only the first carousel 20 and/or only the second carousel 40.

In the following one of the first sterilization device 50 will be described with reference to FIG. 3. The first sterilization devices 50 are substantially constructed in the same manner so that the following description applies to the other first sterilization devices 50 as well. The first sterilization device 50 comprises an electron beam emitter 52 for emitting an electron beam and a power device 66 adapted to provide a high voltage power to the electron beam emitter 52. The electron beam emitter 52 comprises a hermetically sealed vacuum chamber 54, an electron beam generator 56 arranged in the vacuum chamber 54 for generating an electron beam, and an electron exit window 58 at a longitudinal end of the vacuum chamber 54.

The vacuum chamber 54 has housing 60 having an elongate and in particular substantially cylindrical shape. The housing 60 comprises first housing part 62 having a smaller cross-section and a second housing part 64 having a larger cross-section. The electron beam generator 56, which comprises a heatable filament and/or a cathode, is arranged in the second housing part 64. The cylindrical first housing part 62, which may be described as rod-shaped, is adapted to provide an electron acceleration zone between the electron beam generator 56 and the electron exit window 58. The electron exit window 58 is located at an end surface of the first housing part 62. The second housing part 64 contains an electrical interface for connection to the power device 66. The second housing part 64 of the electron beam emitters 52 and the power devices 66 are directly connected to each other and are distributed around the first rotatable shaft 28.

In use, the electron beam is generated by heating the filament. When an electrical current is fed through the filament, the electrical resistance of the filament causes the filament to be heated to a temperature in the order of 2000° C. This heating causes the filament to emit electrons. The electrons are accelerated towards the electron exit window 58 by means of a voltage potential between the cathode and the electron exit window 58 which constitutes the anode. Subsequently, the electrons pass through the electron exit window 58 and continue towards a target area, i.e. in this case the inside of the packaging container 2. Particular, the electrons generate and electron cloud around exit window 58 due to energy loosing scattering effects.

The voltage potential between the cathode and the electron exit window 58 is created for example by connecting the cathode and the filament to the power device 66 and by connecting the housing 60 including the electron exit window 58 to ground. The filament is also connected to the power device 66 for providing an electrical current through the filament. The voltage between the cathode and the electron exit window 58 may be in the order of 75 to 150 kV.

Carrier plate 22 has a plurality of mounting holes arranged with a regular spacing around the rotational axis 4. The electron beam emitters 52 extend through the mounting holes such that the first housing part 62 with exit window 58 protrudes on a first side 23 of carrier plate 22, the lower side. The second housing part 64 as well as the power device 66 is arranged on a second side 24 of carrier plate 22, the upper side. In an alternative embodiment, carrier plate 22 may contain mounting holes suitable to receive also the second housing part 64, thereby separating power device 66 on the upper side from the beam emitters 52. In such embodiment carrier plate 22 also contains a shielding material to prevent radiation emitting into an area above the upper side. Carrier plate 22 comprises steel or another suitable stable material to sustain mechanical forces which can occur during operation.

During a sterilization cycle the first housing part 62 of the sterilization device 50 is inserted into the packaging container 2 through an opening thereof for sterilizing the interior of the packaging container 2.

As illustrated in FIG. 1, a lifting device 48 (only partly shown) is provided for moving the packaging containers 2 along a vertical direction towards and away from the first sterilization device 50. The sterilization device 50 is inserted into a packaging container 2 during the movement of the packaging container 2 together with the guide wheel 42. The guide wheel 42 is rotating synchronously with the carrier wheel 22. Each packaging container 2 is synchronously moved with a first sterilization device 50, thereby keeping the longitudinal axis of the first sterilization device 50 aligned with a longitudinal axis of the packaging container 2.

During the vertical movement of container 2, the inner surface of container 2 is sterilized all the way down to the far end of container 2. The emitted electrons generate and electron cloud around exit window 58 due to energy loosing scattering effects. Every surface part of container 2 passing through said cloud and remaining there for a certain period of time is sterilized. As such electron beam emitter 52 may not only be used to sterilize the inner surface an interior of container 2, but also a portion of the outer surface, particular close to the opening of container 2.

The period of time (sterilization time) a part of the surface of the container has to remain within the electron cloud generated by electron beam emitter 52 must be sufficiently high to eliminate all microbiological substances. In other words each part of the container to be sterilized must be exposed to a sufficiently high dosage. Such dosage (and the corresponding sterilization time) may depend inter alia from the speed of the movement between electron beam emitter 52 and packaging container 2, the electron voltage, the electron current, gas composition and density within and around the container, diameter or distance between of the beam emitter and container, shape of the container and the electron distribution through the exit window.

The first rotatable shaft 28 is constructed as a hollow shaft having a channel 30 extending longitudinally along the shaft. The first rotatable shaft 28 is arranged on the second side 24 of the carrier plate 22, i.e. in this case the upper side. The power device 66 is also arranged on the second side 24 of the carrier plate 22, i.e. on the same side as the first rotatable shaft 28. The channel 30 communicates with the first side 23, i.e. the lower side, of the carrier plate 22. The carrier plate 22 has a central through-hole coaxial with the first rotatable shaft 28.

A distribution chamber 34 is arranged on the first side 23 of the carrier plate 22, at a longitudinal end of the first rotatable shaft 28, in particular under the first rotatable shaft 28. The distribution chamber 34 comprises a substantially cup-shaped housing which preferably completely closes the channel 30 on the first side 23 of the carrier plate 22. In other words, there is no connection between the channel 30 and the sterilization zone which extends on the first side 23 of the carrier plate 22. The distribution chamber 34 has a first opening towards the channel 30 and at least one second opening towards the second side 24 of the carrier plate 22, in particular in a zone radially outside of the first rotatable shaft 28. The carrier plate 22 has a plurality of through-holes 26 in an area surrounding the first rotatable shaft 28 so as to provide a passage between the interior of the distribution chamber 34 and the second side 24 of the carrier plate 22. The distribution chamber 34 provides a passage from the channel 30 to the second side 24 of the carrier plate 22 via the first side 23, wherein the passage along the first side 23 is preferably completely closed by the housing of the distribution chamber 34.

The distribution chamber 34 houses a distribution device 36 for distributing at least one utility such as electricity and/or a cooling fluid to the first sterilization devices 50. The distribution device 36 comprises a swivel in order to distribute the at least one utility from a non-rotating utility line to the rotating sterilization devices 50. The distribution of the utility, in particular electricity, can also be achieved with at least one slip ring. In particular for the protection of the distribution device 36 the housing of the distribution chamber 34 can be provided with a radiation shielding 35, in particular against X-rays which are generated by the electron beam emitters 52. The radiation shielding 35 can be done in a generally known manner, for example using materials such as lead, tungsten or alloys thereof.

The first sterilization devices 50 are continuously operated, i.e. the electron emission is not shut off between sterilization cycles, i.e. it is kept in operation also in between two packaging containers 2 being sterilized by the same sterilization device 50. In a preferred embodiment of the invention the sterilization machine comprises a security unit adapted to keep rotating the first carousel 20 with the first sterilization devices 50 even when the second carousel 40 is standing still, provided that the first sterilization devices 50 are kept in operation. In other words the security device prevents the first carousel 20 standing still while the first sterilization devices are in operation, thereby preventing overheating of the packaging containers 2.

As illustrated in FIG. 1, sterilization apparatus 10 comprises at least one second stationary sterilization device 70 in addition to the plurality of rotating first sterilization devices 50. The first sterilization devices 50 are mainly used for interior sterilization and the at least one second sterilization device 70 is used for partly exterior sterilization of the packaging containers 2. The second sterilization device 70 is preferably arranged such that an overlapping sterilization area is provided where simultaneous exterior and interior sterilization of a packaging container 2 takes place. Sterilization device 70 comprises two beam emitters each having rectangular exit windows. The second sterilization device 70 is arranged along a conveying path of the packaging containers 2. The exit windows of both emitters are facing each other and the packaging containers are passing through an area between the exit windows. Both emitters of stationary sterilization device 70 are slightly tilted or inclined with respect to a planar plane, meaning their exit windows are not parallel to each other, and inclined from a vertical plane. Further, the longitudinal axes of the second sterilization devices are not transversal to the longitudinal axis of containers 2. As a result, the longitudinal axis of the emitters of second sterilization device 70 may have an angle of about 45 degree to 90 degree toward rotational axis 4 or the longitudinal axis of containers 2, preferable between 60 degrees and 80 degree. As a result, when containers enter the area covered by the emitter of sterilization device 70, the outer surface close to the opening of containers 2 is sterilized first. Parts of the outer surface closer to the far end of container 2 are sterilized when passing through the area of both emitters.

By this arrangement the interior and inner surface of container 2 are sterilized first. A common electron cloud and aseptic or sterile zone is generated by one of the first sterilization devices and the second sterilization device at the area where the container enter the second sterilization device 70.

The inventive sterilization apparatus 10 preferably arranged upstream of a filling machine for filling liquid or partly liquid food into packaging containers 2. The packaging containers 2 are conveyed by means of a conveyer 12 which comprises for example a belt or a chain. At the exit of the sterilization machine 10 the packaging containers are sterile and ready for filling.

The device according to the invention can be arranged in an irradiation chamber in a filling machine. The filling machine comprises at least one filling station for filling content into the packaging container and at least one station for sealing the opening after filling. The invention can for example be applied in the sterilization device as described in the international application No. PCT/EP2013/076870 filed by the applicant. During interior sterilization of the packaging containers a relative movement is made between the packaging container and the emitter. A plurality of emitters are provided on a carousel or the like which is adapted to rotate. The packaging containers, which are transported for example via a conveyor, reach the carousel and are attached to one of the (rotating) emitters. During at least a part of one rotation of the carousel, the sterilization of the interior surface of the packaging container takes place. Then the packaging container is removed from the appropriate emitter or from the carousel, respectively, and transported into an aseptic chamber for filling and sealing. The entrance of the aseptic chamber may include emitters for outside sterilization of the packaging containers.

REFERENCE NUMERALS 2 packaging container
4 rotation axis
10 sterilization machine
12 conveyor
14 belt
16 upper support element
18 lower support element
20 first carousel
22 carrier plate
23 first side
24 second side
26 through-hole
28 first rotatable shaft
30 channel
32 first driving device
34 distribution chamber
35 radiation shielding
36 distribution device
40 second carousel
42 guide wheel
44 second rotatable shaft
46 second driving device
48 lifting device 50 first sterilization device
52 electron beam emitter
54 vacuum chamber
56 electron beam generator
58 electron exit window
60 housing
62 first housing part
64 second housing part
66 power device
70 second sterilization device

The invention claimed is:

1. Sterilization apparatus for sterilizing a plurality of packaging containers, the sterilization apparatus comprising:
   a first carousel for supporting a plurality of sterilization devices, the sterilization devices being adapted to sterilize an interior of the packaging containers by electron beam irradiation, and
   a transport system comprising a second carousel for transporting the plurality of packaging container such that each of the plurality of packaging containers is aligned with one of the plurality of sterilization devices supported on the first carousel, the second carousel being coaxial with the first carousel,
   wherein
   the first carousel comprises a first rotatable shaft, and
   the second carousel comprises a separate second rotatable shaft coaxial with the first rotatable shaft.

2. Sterilization apparatus according to claim 1, wherein the sterilization apparatus comprises a first driving device for rotating the first carousel.

3. Sterilization apparatus according to claim 2, wherein the first driving device is coupled by an operative connection to the second rotatable shaft for synchronously driving the first and second rotatable shafts.

4. Sterilization apparatus according to claim 2, wherein the sterilization apparatus comprises a second driving device for rotating the second carousel.

5. Sterilization apparatus according to claim 1, wherein the sterilization apparatus comprises a synchronization means for synchronizing a rotational movement of the first carousel and the second carousel.

6. Sterilization apparatus according to claim 1, wherein the first carousel comprises a carrier plate, attached to the rotatable shaft close to an end portion of the rotatable shaft, wherein the a plurality of sterilization devices are attached to the carrier plate.

7. Sterilization apparatus according to claim 1, wherein the first rotatable shaft is constructed as a hollow shaft having an interior channel for receiving at least one utility line for the sterilization devices.

8. Sterilization apparatus according to claim 1, further comprising:
   a distribution chamber is arranged close to an end portion of the first rotatable shaft facing the second rotatable shaft.

9. Sterilization apparatus according to claim 8, wherein the distribution chamber is arranged on a first side of the carrier plate and the plurality of sterilization devices are mounted on a second side of the carrier plate.

10. Sterilization apparatus according to claim 9, wherein the distribution chamber comprise at least one opening towards the second side of the carrier plate opposite the first side.

11. Sterilization apparatus according to claim 8, further comprising:
    a distribution device for distributing at least one utility to the sterilization devices, arranged within the distribution chamber.

12. Sterilization apparatus according to claim 11, wherein the distribution device includes a swivel.

13. Sterilization apparatus according to claim 8, wherein the distribution chamber comprises a radiation shielding, in particular against X-rays.

14. Sterilization apparatus according to claim 1, wherein at least one second sterilization device is arranged between the first carousel and the second carousel for sterilizing an outer surface of the packaging containers.

15. Sterilization apparatus according to claim 14, wherein the second sterilization device extends at least partly between the first rotatable shaft and the second rotatable shaft.

16. Sterilization apparatus according to claim 14, wherein the second sterilization device has a longitudinal axis extending substantially transversely to the rotation axis of the first rotatable shaft and/or the second rotatable shaft.

17. Method for sterilizing a plurality of packaging containers, in particular with a sterilization apparatus according to claim 1, the method comprising:
    rotating a first carousel supporting a plurality of sterilization devices which are adapted to sterilize an interior of the packaging containers by electron beam irradiation, and
    transporting the packaging containers by a transport system comprising a second carousel such that each of the plurality of packaging containers is aligned with one of the plurality of sterilization devices supported on the first carousel, the second carousel being coaxial with the first carousel,
    wherein
    the first carousel comprises a first rotatable shaft,
    the second carousel comprises a separate second rotatable shaft coaxial with the first rotatable shaft, and
    the first carousel is rotated by a first driving device connected to the first rotatable shaft for rotation thereof.

18. Sterilization apparatus according to claim 1, wherein the first rotatable shaft is configured to be driven by a first driving device and the second rotatable shaft is configured to be driven by a second driving device, the first and second driving devices being mounted outward from a sterilization area defined between the first carousel and the second carousel.

19. Sterilization apparatus according to claim 1, further comprising a lifting device moving the plurality of packaging containers along a vertical direction towards and away from the first carousel supporting the plurality of sterilization devices such that the sterilization devices are inserted into the packaging containers.

* * * * *